(12) United States Patent
Tang

(10) Patent No.: US 8,317,740 B1
(45) Date of Patent: Nov. 27, 2012

(54) DRUG PRESSURING AND DELIVERING SYSTEM WITH INTERNAL QUANTITATIVE PUSHER

(75) Inventor: James Tang, Taipei (TW)

(73) Assignee: Gold Nanotech, Inc. (TW)

( * ) Notice: Subject to any disclaimer, the term of this patent is extended or adjusted under 35 U.S.C. 154(b) by 0 days.

(21) Appl. No.: 13/137,943

(22) Filed: Sep. 22, 2011

(30) Foreign Application Priority Data

May 27, 2011 (TW) .............................. 100118572 A

(51) Int. Cl.
*A61M 5/30* (2006.01)
*A61M 1/00* (2006.01)

(52) U.S. Cl. .............................. 604/71; 604/24; 604/152

(58) Field of Classification Search ..................... 604/19, 604/23, 24, 68–72, 151, 152; 128/200.14–200.19, 128/200.21–200.23, DIG. 1
See application file for complete search history.

(56) References Cited

U.S. PATENT DOCUMENTS

| | | | | |
|---|---|---|---|---|
| 3,202,151 A | * | 8/1965 | Kath | 604/71 |
| 4,529,401 A | * | 7/1985 | Leslie et al. | 604/131 |
| 5,049,125 A | * | 9/1991 | Accaries et al. | 604/70 |
| 5,515,842 A | * | 5/1996 | Ramseyer et al. | 128/200.18 |
| 5,993,412 A | * | 11/1999 | Deily et al. | 604/68 |
| 7,927,307 B2 | * | 4/2011 | D'Antonio et al. | 604/152 |
| 8,221,347 B2 | * | 7/2012 | Toles et al. | 604/70 |

* cited by examiner

*Primary Examiner* — Matthew F Desanto

(57) ABSTRACT

A drug pressuring and delivering system has an internal quantitative pusher for providing stable and precise drug delivery, and a drug pressuring and delivering device for introducing a compression gas for pressuring and ejecting a drug into an atomized drug. The quantitative pusher adopts a bidirectional motor for driving a screw rod to rotate forward or reversely to push the push rod forward or backward, such that the drug is delivered through a solenoid and a drug delivering needle in a cylinder drug delivering pipe and then quantitatively delivered to a drug delivery pressuring tube. In addition, an introduced mainstream gas in the drug delivery pressuring tube forms a gas-liquid mixing and pressuring action to achieve the precisely quantitative and uniform atomization high speed ejection function. Also, all members of the invention can be assembled/disassembled, so that the damaged or contaminated members can be detached, cleaned or replaced.

5 Claims, 9 Drawing Sheets

DRUG PRESSURING AND DELIVERING SYSTEM WITH INTERNAL QUANTITATIVE PUSHER

BACKGROUND OF THE INVENTION (1) Field of the Invention

The invention relates to a quantitative drainage atomizing and ejecting system for quantitatively delivering a drug in an electrically powered mode, and the drug is pressured, atomized and ejected by a delivery system, which can eject the atomized drug at a high speed. The drug may be freely replaced with a new one. Thus, a drug pressuring and delivering system having the internal quantitative pusher can be obtained to achieve the quantitative delivery and pressuring and atomizing effects.

(2) Description of the Prior Art

At present, there are many kinds of injectors for cosmetology and medicine, but the real needleless dermis drug delivery system is rarely seen. Each of most of the currently used liquid injectors has a gun body, which has a chamber or housing for loading the drug and is connected to a high-pressure gas source. According to the high-pressure principle, the injector is pressed on the patient's skin. When the trigger is pushed, the drug is ejected from a muzzle in a columnar manner and injected into the skin to achieve the delivery effect. However, the skin wound and pain are caused, and the whole sterilization and disinfection processes have to be performed if the drug has to be replaced with a new one. In another aspect, the pressure directly atomizes and ejects the drug. This delivery method still cannot achieve the speed requirement and the precise and quantitative requirements for the dermis delivery.

The needleless injector having the convenience and utility becomes the trend of the future development. However, the current structure designs still have the following drawbacks to be improved.

First, the typical needleless liquid drug delivering device is still mainly based on the liquid column delivery.

Second, the typical needleless liquid drug atomizing and delivering device generates the non-uniform particles, cannot work precisely and quantitatively, and cannot achieve the ejecting speed higher than 100 m/sec.

Third, the typical drug delivering device is usually not detachable, and thus cannot be disassembled for cleaning and maintenance. More particularly, the cleanness inside the tube cannot be improved.

Fourth, the typical liquid atomizer has the inconvenience in charging the drug or mounting/replacing the bottle because the processes are time-wasting and labor-wasting. The previously used drug is often remained in the tube. If the tube is not properly cleaned or another drug is used in this apparatus, the risk of curing the patient tends to occur.

In view of the associated problems induced by the design defects of the prior art, the present inventor has paid attention to the research, development, improvement and tests, and thus developed this drug pressuring and delivering system with internal quantitative pusher for the benefit of industry and society.

SUMMARY OF THE INVENTION

An object of the invention is to provide a drug pressuring and delivering system with an internal quantitative pusher to achieve the quantitative and continuous effects of delivering the drug more precisely and stably.

Another object of the invention is to provide a detachable drug pressuring and delivering system with an internal quantitative pusher, wherein elements of the system can be detached, cleaned or replaced.

In one preferred embodiment designed according to the above-mentioned objects, a drug pressuring and delivering system is provided. The drug pressuring and delivering system includes a drug pressuring and delivering device and a quantitative pusher.

The drug pressuring and delivering device includes one set of an upper cover and a base matching with each other, a drug delivery pressuring tube having a circumferential surface formed with a combination portion, and a fixed receptacle externally connected to a mainstream gas source in the form of a tube, so that the mainstream gas source is inputted at the high pressure.

The quantitative pusher includes one set of an upper cover and a housing seat matching with each other, a screw rod quantitative pusher, a cylindrical drug delivering pipe and a baffle. The screw rod quantitative pusher has one end connected to a screw rod of a bidirectional motor and the other end fixed to a movable block. A fixing sheet is fixed to one side of the movable block so that a micro switch and a circuit board can be electrically connected thereto and disposed thereon. A push rod holding device is pivotally mounted on the movable block. The cylindrical drug delivering pipe is composed of a drug delivering needle and a push rod. A front end of the drug delivering needle is clamped and positioned by a receptacle fixed to a combination portion. The baffle is disposed between the cylindrical drug delivering pipe and the screw rod quantitative pusher and has a surface formed with a supporting seat, an axial guiding slot and a radial accommodating slot connected to the axial guiding slot. The supporting seat is provided such that the drug delivering needle of the cylindrical drug delivering pipe is stably disposed. The accommodating slot allows the push rod holding device to penetrate therethrough and makes an engagement portion, pivotally connected to the movable block, to move in the guiding slot.

In operation, the circuit board controls the bidirectional motor to drive the screw rod to rotate forward or reversely and to drive the push rod holding device to push or pull the push rod to move forward or backward, such that the drug in the cylindrical drug delivering pipe is delivered through the solenoid and the drug delivering needle and then quantitatively delivered into the drug delivery pressuring tube, and the effects of quantitatively delivering, pressuring and ejecting the drug can be achieved.

The present invention will become more fully understood from the detailed description given hereinbelow and the accompanying drawings which are given by way of illustration only, and thus are not limitative of the present invention.

Further aspects, objects, and desirable features of the invention will be better understood from the detailed description and drawings that follow in which various embodiments of the disclosed invention are illustrated by way of examples.

DETAILED DESCRIPTION OF THE PREFERRED EMBODIMENTS

Figure 1:
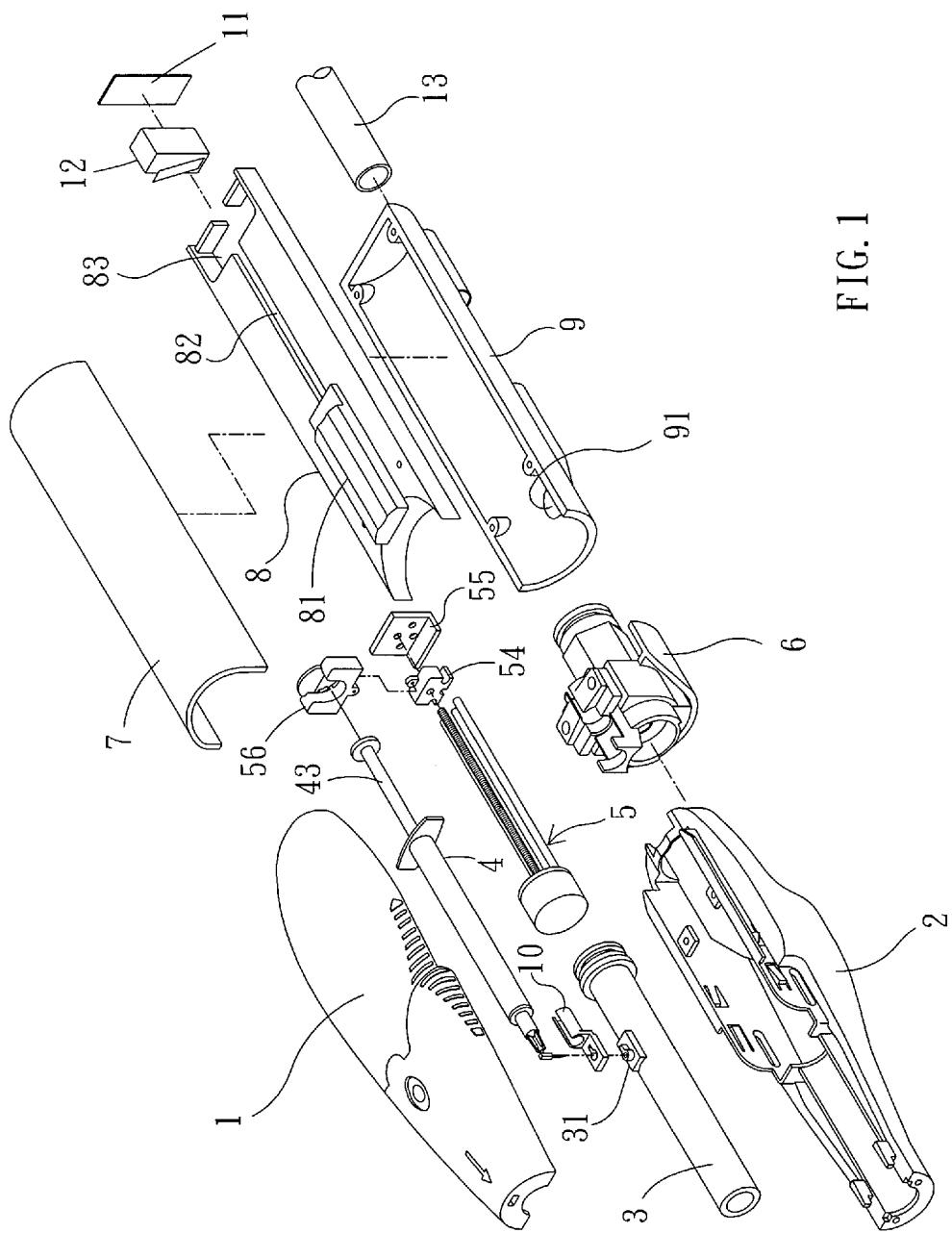
FIG. 1 is an exploded view showing a drug pressuring and delivering system with an internal quantitative pusher according to a preferred embodiment of the invention.

FIG. 1 is an exploded view showing a drug pressuring and delivering system with an internal quantitative pusher according to a preferred embodiment of the invention. Referring to the drawing, the drug pressuring and delivering system includes a drug pressuring and delivering device and a quantitative pusher.

The drug pressuring and delivering device includes one set of an upper cover (1) and a base (2), a drug delivery pressuring tube (3) and a fixed receptacle (6).

The upper cover (1) and the base (2) matching with each other can be connected together by the pivotal connection or tongue connection so that the upper cover (1) can be opened and closed to facilitate the element cleaning, updating and replacing.

The drug delivery pressuring tube (3) is manufactured, based on the Venturi tube principle, to have two ends formed with tapered holes connected together, and a middle portion of the drug delivery pressuring tube (3) is formed with a throat. One of the tapered holes serves as a mainstream gas inlet, and the other of the tapered holes serves as a drug outlet. A circumferential surface of the drug delivery pressuring tube (3) is formed with a combination portion (31).

The fixed receptacle (6) is externally connected to a mainstream gas source in the form of a tube, so that the mainstream gas source is inputted at the high pressure.

Figure 5:
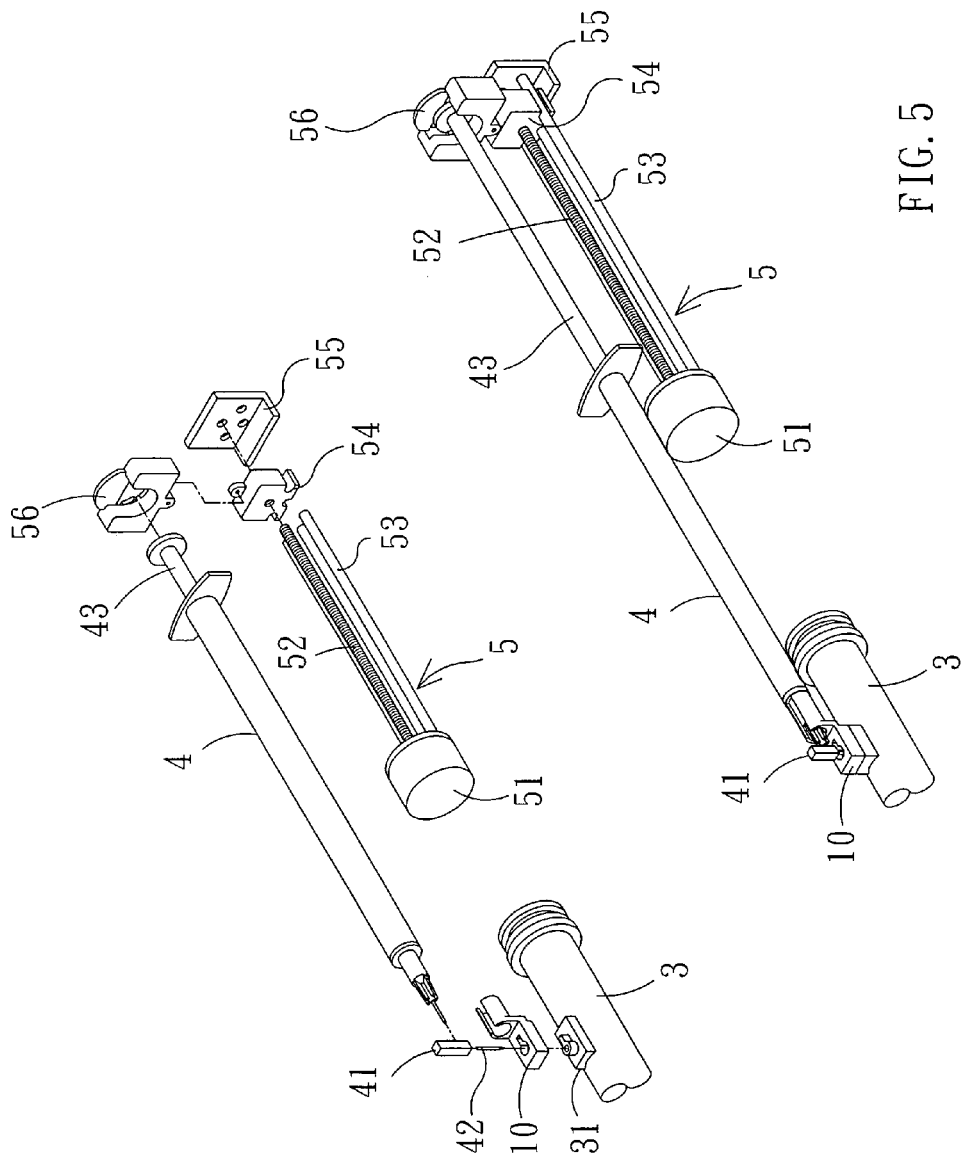
FIG. 5 is an exploded view showing a quantitative pusher in the drug pressuring and delivering system according to a preferred embodiment of the invention.

As shown in FIG. 5, the quantitative pusher includes one set of an upper cover (7) and a housing seat (9), a cylindrical drug delivering pipe (4), a screw rod quantitative pusher (5) and a baffle (8).

The upper cover (7) and the housing seat (9) match with each other. The housing seat (9) has a chamber and one end connected to the fixed receptacle (6). A circumferential surface of the housing seat (9) near the fixed receptacle (6) is formed with a through hole (91), through which a mainstream gas delivering pipe (13) passes for positioning.

The cylindrical drug delivering pipe (4) is composed of a drug delivering needle (42) and a push rod (43) in the form of a cylinder. A solenoid (41) is disposed on a front end (outlet end) of the drug delivering needle (42), which is clamped and positioned by a receptacle (10) fixed to the combination portion (31). The solenoid (41), having an electrically controlled opening-closing function, prevents a gas and a drug in the pressuring tube from flowing back.

Figure 6:
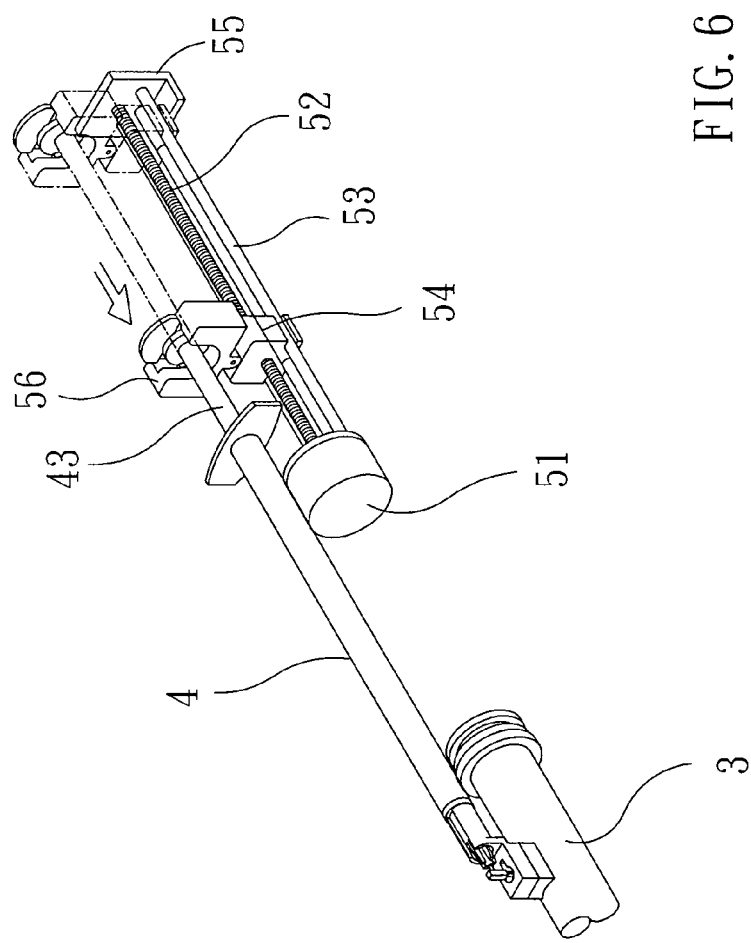
FIG. 6 is a schematic illustration showing an operation of the quantitative pusher according to the content of FIG. 5.
Figure 7:
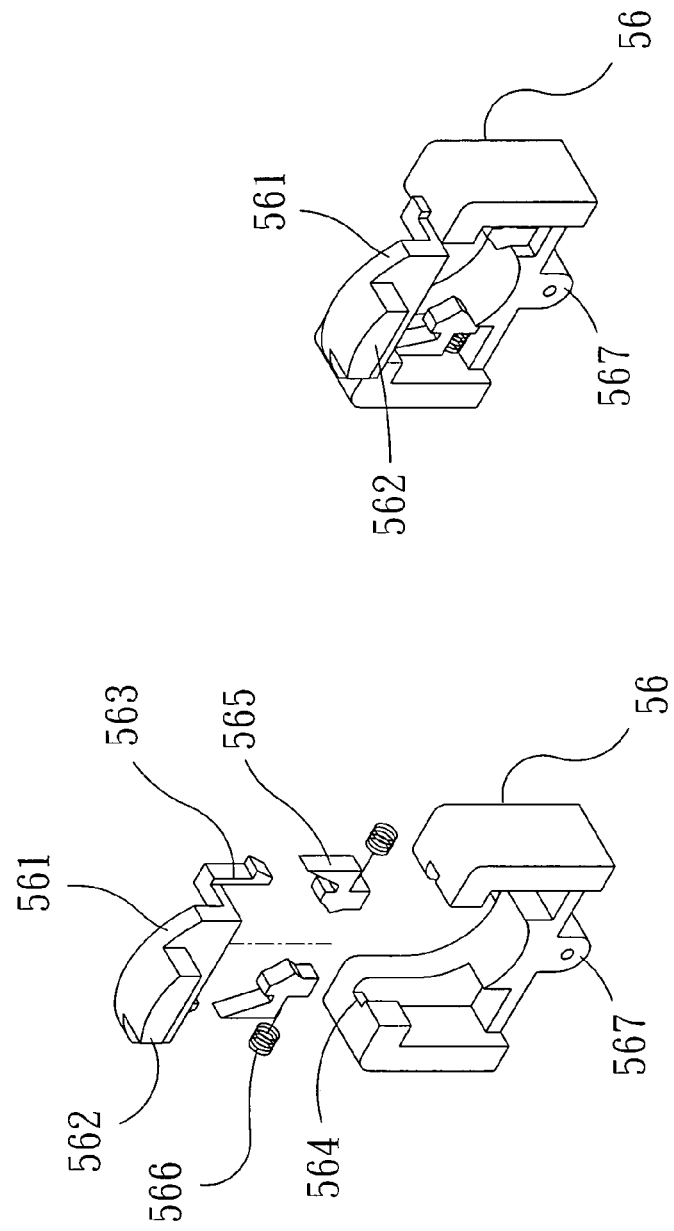
FIG. 7 is a decomposed and assembled view showing a structure of a push rod holding device in a drug pressuring and delivering system with an internal quantitative pusher according to a preferred embodiment of the invention.
Figure 8:
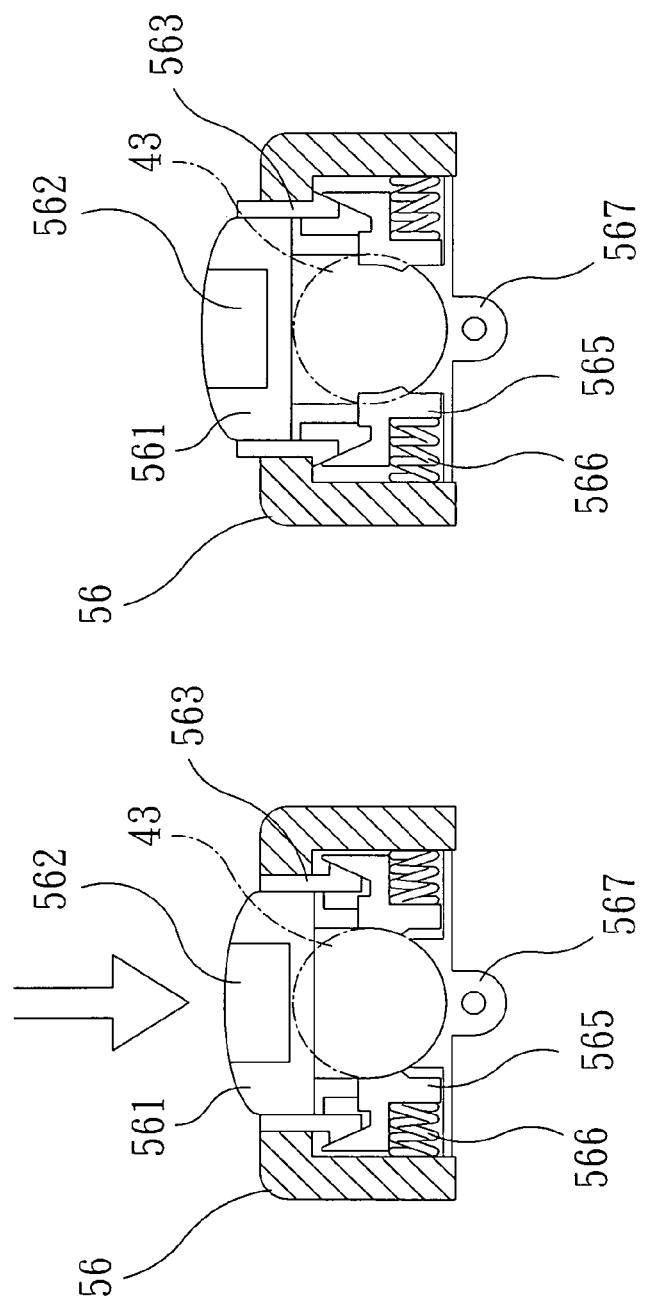
FIG. 8 is a schematic illustration showing an operation of the push rod holding device according to the content of FIG. 7.

The screw rod quantitative pusher (5), disposed between the upper cover (7) and the housing seat (9), has one end connected to a screw rod (52) and a movable guiding rod (53) of a bidirectional motor (51), disposed in parallel, and the other end fixed to a movable block (54). A fixing sheet (55) is fixed to one side of the movable block (54) so that a micro switch (12) and a circuit board (11) can be electrically connected thereto and disposed thereon. A push rod holding device (56) is pivotally mounted on the movable block (54) to provide the combination and mounting for the distal end of the push rod (43). As shown in FIG. 6, the circuit board (11) controls the bidirectional motor (51) to drive the screw rod (52) to rotate forward or reversely to drive the push rod holding device (56) to push or pull the push rod (43) to quantitatively move forward or backward. The detailed structure and operation features of the push rod holding device (56) can be seen in FIGS. 7 and 8. As shown in FIG. 7, the top of the body of the push rod holding device (56) has a half-moon opening, and two guiding slots (564) formed on two opposite inner sides thereof, so that a movable presser (561) can be embedded with the guiding slots (564). The bottom of the body of the push rod holding device (56) has a projecting engagement portion (567). One side of the top of the movable presser (561) has a projection (562) for triggering the micro switch (12), and two lateral sides of the movable presser (561) are formed with opposite supports (563) with hooks. A stopper sheet (565) and an elastic member (566) are disposed in the guiding slot (564) so that two supports (563) are linked up to push the stopper sheet (565) outward when the movable presser (561) is pressed down. At this time, the distal end of the push rod (43) can be engaged or disengaged. When the movable presser (561) is released, the two stopper sheets (565) are pushed by the elastic force of the elastic member (566) and restore and push the movable presser (561) to restore upward. At this time, the two stopper sheets (565) have the clamping effect, as shown in FIG. 8. Of course, the adopted clamping and releasing actions of the stopper sheet (565) and the elastic member (566) are not restricted thereto, and may also be integrally made of an elastic plastic member.

The baffle (8) is disposed between the cylindrical drug delivering pipe (4) and the screw rod quantitative pusher (5), and has a surface formed with a supporting seat (81), an axial guiding slot (82) and a radial accommodating slot (83) connected to the axial guiding slot (82). The supporting seat (81) is provided such that the drug delivering needle (42) of the cylindrical drug delivering pipe (4) can be stably disposed. The accommodating slot (83) can allow the push rod holding device (56) to penetrate therethrough, and enable an engagement portion (567), pivotally connected to the movable block (54), to move in the guiding slot (82).

Figure 2:
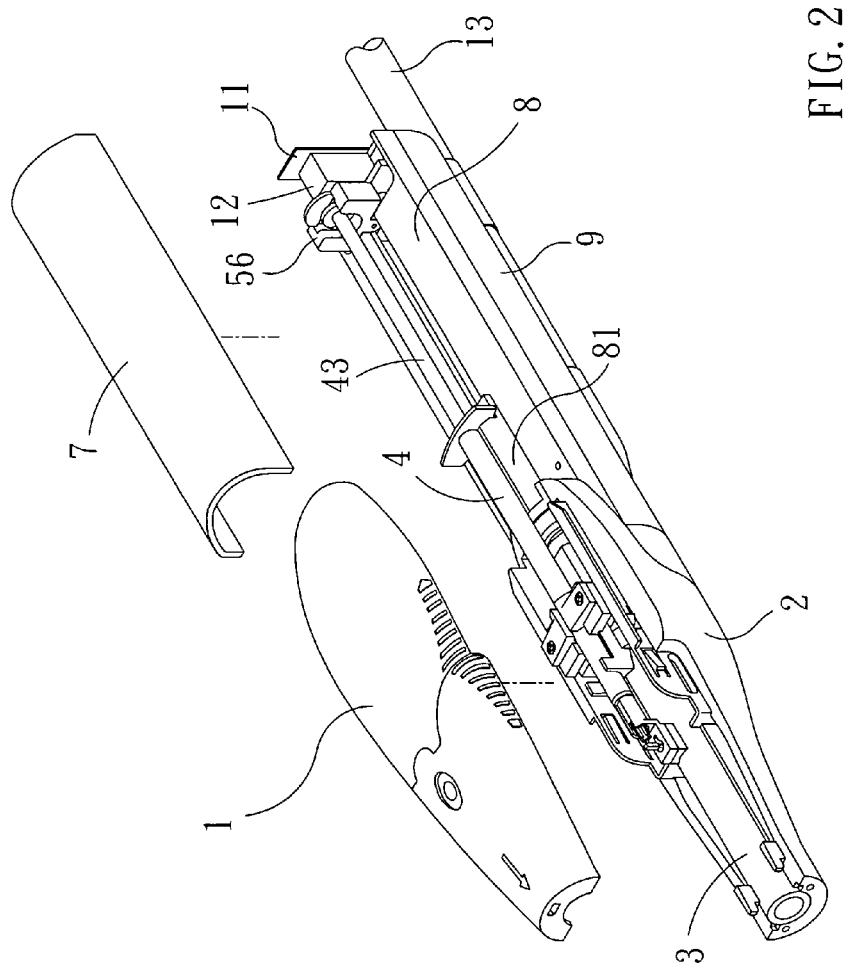
FIG. 2 is a schematically decomposed illustration showing the substantial structure according to the content of FIG. 1.

As shown in FIG. 2, when the elements of the drug pressuring and delivering system of the invention are to be cleaned, updated or replaced, each of the set of the upper cover (1) and the base (2) of the drug pressuring and delivering device and the set of the upper cover (7) and the housing seat (9) of the quantitative pusher are connected together by the pivotal connection or tongue connection, so the elements can be simply and conveniently disassembled. Only the upper cover (1) or (7) needs to be opened so that the element cleaning, updating or replacing can be performed.

Figure 3:
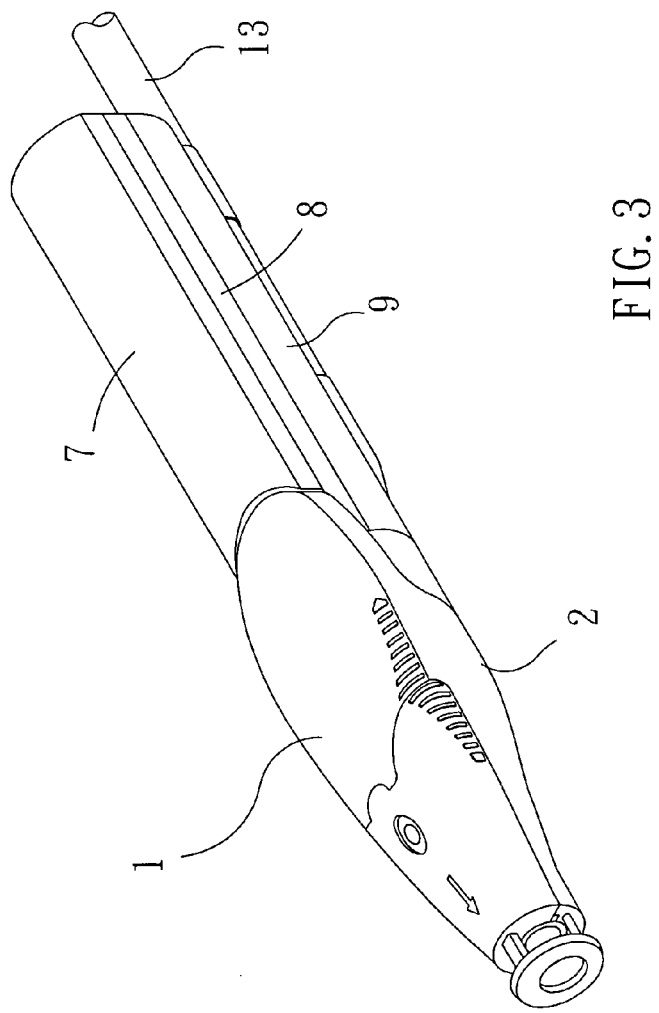
FIG. 3 is an exterior view showing the drug pressuring and delivering system with the internal quantitative pusher according to the content of FIG. 1.

FIG. 3 is an exterior view showing the completely assembled drug pressuring and delivering system with the internal quantitative pusher according to the content of FIG. 1. As shown in FIG. 3, the longitudinal drug pressuring and delivering system can be easily held.

Figure 4:
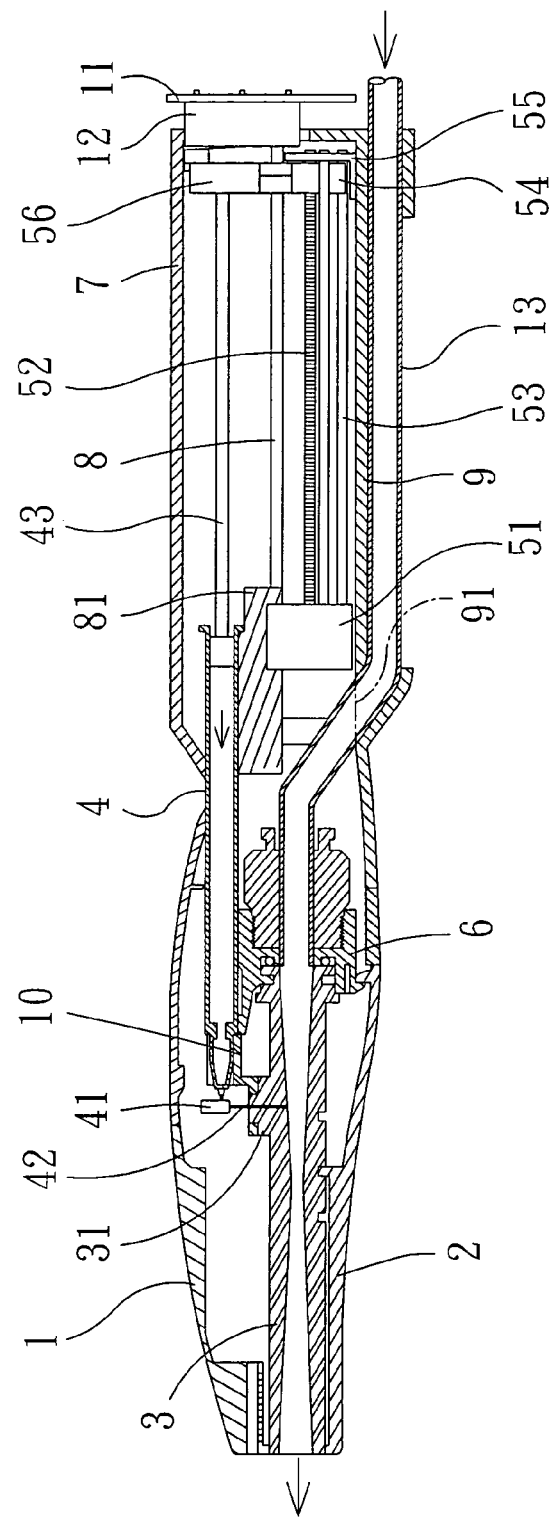
FIG. 4 is a cross-sectional view showing the drug pressuring and delivering system with the internal quantitative pusher according to the content of FIG. 1.

FIG. 4 is a cross-sectional view showing the overall drug pressuring and delivering system with the internal quantitative pusher according to the content of FIG. 1. As shown in FIG. 4, the quantitative pusher is connected to the rear end of the drug pressuring and delivering device, and the fixed receptacle (6) of the drug pressuring and delivering device is connected to the mainstream gas delivering pipe (13) disposed below or on the bottom of the housing seat (9) so that the external mainstream gas source can be inputted at the high pressure.

The quantitative pusher is disposed above the mainstream gas delivering pipe (13) so that the circuit board controls the bidirectional motor (51) to drive the screw rod (52) to rotate forward or reversely and to drive the push rod holding device (56) to push or pull the push rod (43) to move forward or backward, such that the drug is quantitatively delivered into the drug delivery pressuring tube (3) from the drug delivering needle (42) in the cylindrical drug delivering pipe (4), and the effects of quantitatively delivering, pressuring and ejecting the drug can be achieved.

Figure 9:
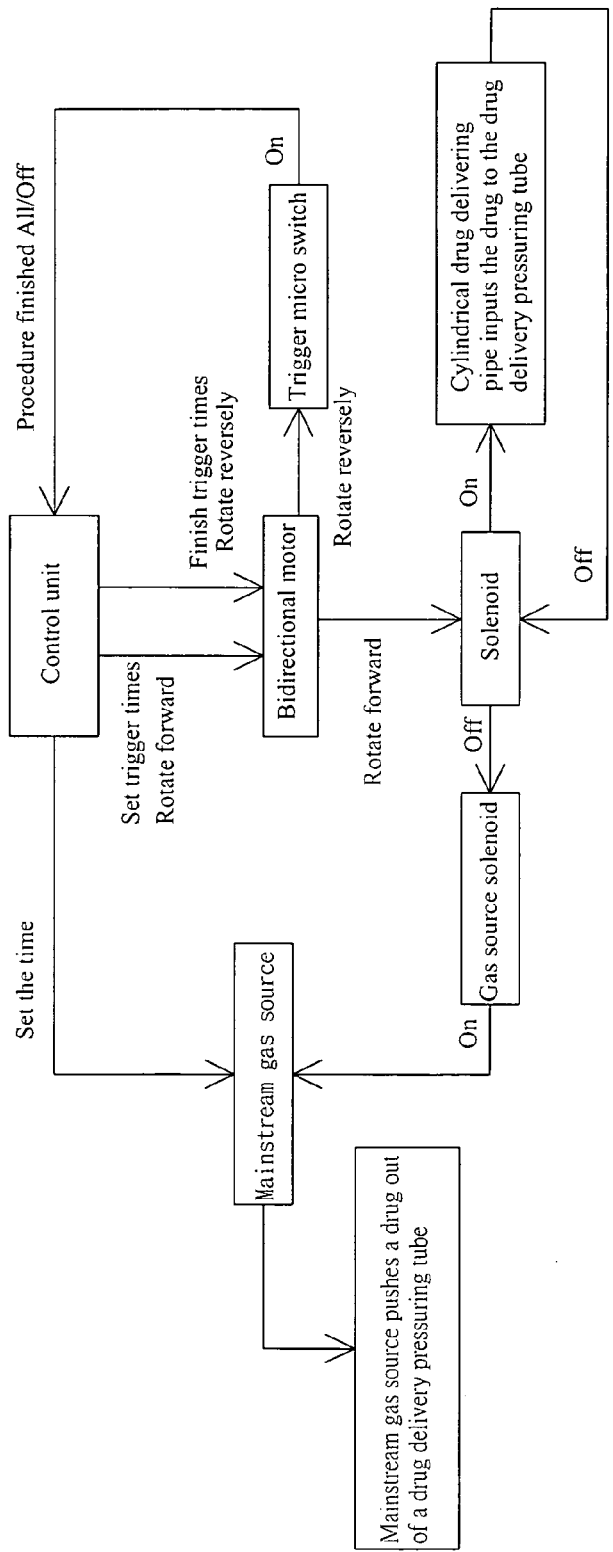
FIG. 9 is an electrical control flow chart showing a drug pressuring and delivering system with an internal quantitative pusher according to a preferred embodiment of the invention.

FIG. 9 is an electrical control flow chart showing a drug pressuring and delivering system with an internal quantitative pusher according to a preferred embodiment of the invention. The operation flow will be described with reference to FIGS. 4 and 9.

First, the control unit is used to set various required parameter options, such as the drug push dosage, the mainstream gas source push time, the triggering interval and the like.

Next, the solenoid (41) is turned on and the bidirectional motor (51) is driven to rotate forward to drive the screw rod (52) to push the push rod (43), such that the drug in the cylindrical drug delivering pipe (4) is delivered into the drug delivery pressuring tube (3) with a predetermined quantity. Meanwhile, the solenoid (41) is turned off, and the mainstream gas source and the gas source solenoid are turned on to introduce the gas into the drug delivery pressuring tube (3) through the mainstream gas delivering pipe (13), so that the quantitative drug is mixed with the gas and pressured and ejected in an atomized manner.

After one time of drug injection is finished, the control unit drives the bidirectional motor (51) to reverse and drive the screw rod (52) to pull the push rod (43) to restore until the projection (562) of the movable presser (561) touches the micro switch (12).

The operations are repeated until the drug is completely exhausted. Then, the drug can be replaced with a new one.

According to the above-mentioned description, it is stated that the invention adopts the electrically controlled method to quantitatively and continuously input the drug very precisely and stably. Meanwhile, the mainstream gas source for controlling the compression is introduced into the drug pressuring and delivering device, so that the drug quantitatively inputted into the drug pressuring and delivering device is mixed with the mainstream gas and pressured and ejected, the drug can be atomized and ejected at the high speed and in the precisely quantitative manner.

In summary, the drug pressuring and delivering system with the internal quantitative pusher according to the invention can achieve the predicted object and effect, and has not been disclosed in the associated data so that this application is properly filed.

New characteristics and advantages of the invention covered by this document have been set forth in the foregoing description. It is to be expressly understood, however, that the drawings are for the purpose of illustration only and are not intended as a definition of the limits of the invention. Changes in methods, shapes, structures or devices may be made in details without exceeding the scope of the invention by those who are skilled in the art. The scope of the invention is, of course, defined in the language in which the appended claims are expressed.

What is claimed is:

1. A drug pressuring and delivering system, comprising:
a drug pressuring and delivering device, which comprises one set of an upper cover and a base matching with each other, a drug delivery pressuring tube having a circumferential surface formed with a combination portion, and a fixed receptacle externally connected to a mainstream gas source in the form of a tube, so that the mainstream gas source is inputted at a high pressure; and
a quantitative pusher, which comprises one set of an upper cover and a housing seat matching with each other, a screw rod quantitative pusher, a cylindrical drug delivering pipe and a baffle, wherein the screw rod quantitative pusher has one end connected to a screw rod of a bidirectional motor and the other end fixed to a movable block, a fixing sheet is fixed to one side of the movable block so that a micro switch and a circuit board can be electrically connected thereto and disposed thereon, a push rod holding device is pivotally mounted on the movable block, the cylindrical drug delivering pipe is composed of a drug delivering needle and a push rod, a front end of the drug delivering needle is clamped and positioned by a receptacle fixed to a combination portion, the baffle is disposed between the cylindrical drug delivering pipe and the screw rod quantitative pusher and has a surface formed with a supporting seat, an axial guiding slot and a radial accommodating slot connected to the axial guiding slot, the supporting seat is provided such that the drug delivering needle of the cylindrical drug delivering pipe is stably disposed, and the accommodating slot allows the push rod holding device to penetrate therethrough and makes an engagement portion, pivotally connected to the movable block, to move in the guiding slot,
wherein the circuit board controls the bidirectional motor to drive the screw rod to rotate forward or reversely to drive the push rod holding device to push or pull the push rod forward or backward, so that quantitative delivery and drug pressuring and ejecting are achieved.

2. The system according to claim 1, wherein a top of a body of the push rod holding device has a half-moon opening, and two guiding slots formed on two opposite inner sides thereof, so that a movable presser can be embedded with the guiding slots, a bottom of the body of the push rod holding device has a projecting engagement portion, one side of a top of the movable presser has a projection for triggering the micro switch, two lateral sides of the movable presser are formed with opposite supports with hooks, and a stopper sheet and an elastic member are disposed in the guiding slot.

3. The system according to claim 2, wherein the stopper sheet and the elastic member of the push rod holding device are integrally made of a plastic material.

4. The system according to claim 1, wherein a solenoid, having an electrically controlled opening-closing function, is disposed on an outlet end of the drug delivering needle, to prevent a gas and a drug in the pressuring tube from flowing back.

5. The system according to claim 1, wherein each of the set of the upper cover and the base of the drug pressuring and delivering device and the set of the upper cover and the housing seat of the quantitative pusher are connected together by pivotal connection or tongue connection, so that element cleaning, updating or replacing can be performed conveniently.

* * * * *